US00PP26894P2

(12) United States Plant Patent
Hansen

(10) Patent No.: US PP26,894 P2
(45) Date of Patent: Jun. 28, 2016

(54) ***HEUCHERA* PLANT NAMED 'GRAPE EXPECTATIONS'**

(50) Latin Name: ***Heuchera* hybrid**
Varietal Denomination: Grape Expectations

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 87 days.

(21) Appl. No.: 14/121,450

(22) Filed: Sep. 8, 2014

(51) Int. Cl.
*A01H 5/12* (2006.01)

(52) U.S. Cl.
USPC ..... Plt./440

(58) Field of Classification Search
USPC ..... Plt./440
See application file for complete search history.

(56) References Cited

PUBLICATIONS

Mamajack's Jun. 17, 2014 retrieved on Jan. 28, 2016, retrieved from the Internet at <http://cubits.org/notfortheserious/thread/view/79224/> 8 pp.*

Perennial Resource retrieved on Jan. 28, 2016, retrieved from the Internet at <http://www.perennialresource.com/plants/general-perennial/2446_heuchera-grape-expectations-ppaf.aspx> 3 pp.*

* cited by examiner

*Primary Examiner* — June Hwu

(57) ABSTRACT

The new and distinct hybrid of *Heuchera* plant named 'Great Expectations' with foliage color that changes throughout the year emerging in the spring with leaves of vibrant grape purple above, then developing a silvery surface over darker greyed purple, and topped with branched panicles of compact near white flowers. Foliage then develops purplish-silver between the veins, and by late season intensifying to deep purple and decreasing the silvery regions between the veins. The near white colored campanulate flowers appear on a branched panicle effective over a long period. The new plant is vigorous, compact in habit and tolerates heat and humidity well.

1 Drawing Sheet

Botanical denomination: *Heuchera* hybrid.
Cultivar designation: 'Grape Expectations'.

BACKGROUND OF THE INVENTION

The present invention relates to a new and distinct cultivar of Coral Bells in the Saxifragaceae family and given the cultivar name of 'Grape Expectations'. *Heuchera* 'Grape Expectations' was hybridized by the inventor on Jan. 24, 2012 at a nursery in Zeeland, Mich., USA an initially assigned the breeder code H12-107-02. The seed or female parent was a selected, unreleased, proprietary seedling known as *Heuchera* K10-70-99 (not patented) and the pollen or male parent was a selected, unreleased, proprietary seedling known as *Heuchera* K9-56-06 (not patented). The new invention has a mixture of *Heuchera americana, H. brizoides, H. micrantha* and *H. villosa* in the pedigree.

*Heuchera* 'Grape Expectations' was first selected in the spring of 2012 and passed final evaluation in the fall of 2013 from among thousands of other seedlings from the same cross and hundreds of other crosses. *Heuchera* 'Grape Expectations' has been asexually propagated by division at the same nursery in Zeeland, Mich. and by careful tissue culture propagation, and the resultant plants have remained stable and continued to exhibit the same characteristics as the original plant for multiple generations.

BRIEF SUMMARY OF THE INVENTION

In comparison to the parents, *Heuchera* 'Grape Expectations' has more purplish-red foliage and more contrasting silver variegation and flowers of near white rather than the dark purple foliage with flowers of pinkish yellow to cream.

*Heuchera* 'Grape Expectations' is probably most similar to 'Plum Royale', but the new plant differs in having more contrasting silver variegation and flatter leaf blades. The nearest comparison cultivars are *Heuchera* 'Plum Royale' U.S. Plant Pat. No. 20,935 and 'Plum Pudding' (not patented). *Heuchera* 'Plum Royale' flowers are more pink and the flowers of 'Plum Pudding' are more cream-colored than the near white of 'Grape Expectations', and the flowers of 'Grape Expectations' are larger than either of the two nearest comparison cultivars. The foliage of 'Plum Pudding' is less reddish purple, less intense silver variegation, with more rippling or cupped flat leaf blades than the new plant. The foliage of 'Plum Royale' is more lustrous than the new plant.

*Heuchera* 'Grape Expectations' differs from its parents as well as all other Coral Bells known to the applicant in the following combined traits:

1. The foliage color of 'Grape Expectations' changes throughout the year depending on the temperature and rate of growth emerging vibrant grape purple.
2. Mid-summer foliage then develops a purplish-silver between the veins and toward fall develops a base of deep purple.
3. The creamy-colored campanulate flowers appear on branched panicles beginning late spring and effective over a long period.
4. The new plant is vigorous, compact in leaf habit and tolerates heat and humidity.

BRIEF DESCRIPTION OF THE DRAWINGS

The photographs of the new plant demonstrate the overall appearance of the plant including the unique traits. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
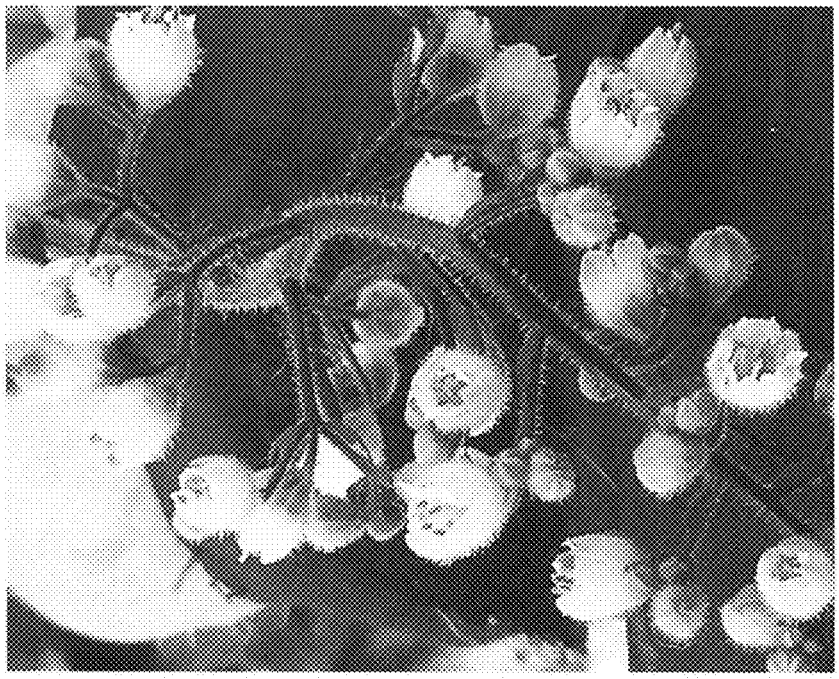
FIG. 1 shows a close-up of the flowers and buds.
Figure 2:
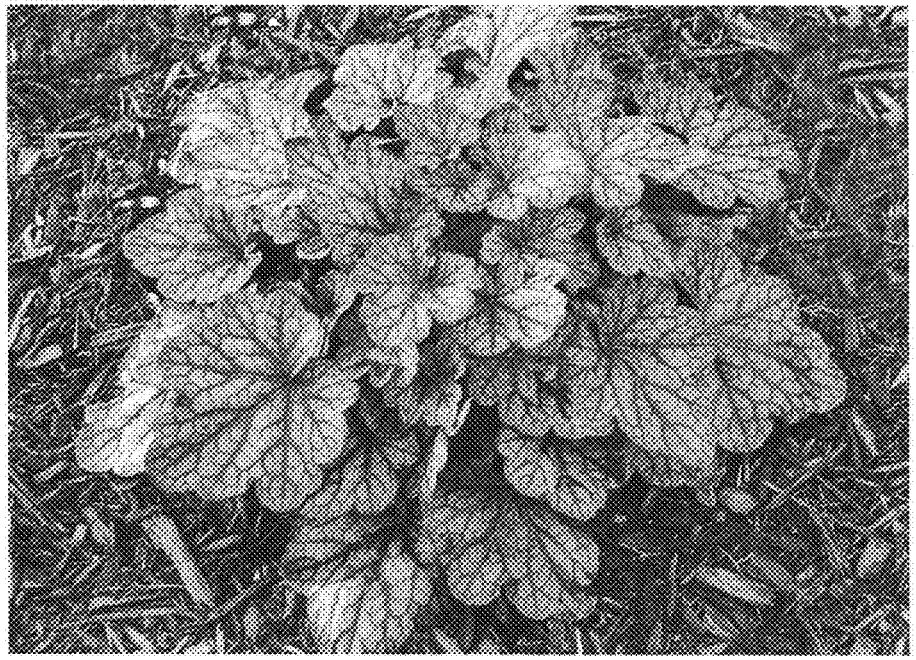
FIG. 2 shows a two-year old plant with late winter and early spring foliage.

The following description is based on a two-year old plant growing in a lightly shaded greenhouse in Zeeland, Mich., USA. The new plant has not been grown under all possible environments and may phenotypically appear different under different conditions such as light, temperatures, fertilizer, and water, without any difference in genotype. The color descriptions used are from the 2001 edition of The Royal Horticultural Society Colour Chart except where common dictionary terms are used.

Parentage: Female (seed parent)—a selected, unreleased, proprietary seedling known as Heuchera K10-70-99 (not patented) and the pollen or male parent was a selected, unreleased, proprietary seedling known as *Heuchera* K9-56-06 (not patented).

Plant habit: Hardy herbaceous perennial with basal rosette of foliage; mounded foliage about 30 cm tall and 46 cm in diameter.

Roots: Fibrous, finely branched.

Growth rate: Rapid, rooting from cutting in two weeks and finishing in three-liter container in about 3 months.

Foliage: Cordate; crenate and pubescent margins, sparsely hirsutulous above and below; palmately lobed with three to five shallowly dissected main lobes each having three or more sub-lobes; rounded apex and cordate base with overlapping lobes; indentations shallow; blade average about 12.0 cm long and 11.5 cm wide; leaf color is variable with season.

*Leaf color*.—Spring young emerging leaves adaxial nearest RHS 187A with little or no silver and dark green between RHS N189A and RHS N187A surrounding the veins, spring young emerging leaves abaxial between RHS 187A and RHS 187B; mid-season flowering time leaves adaxial between RHS N187B and RHS N187C with area surrounding veins of greyed-purple nearest RHS N186A, and some lighter tinting of between RHS N186B and RHS N186C with pinkish-silver cast of mixture of RHS N187C and RHS 186C; abaxial mid-season leaves between RHS 187A and RHS N186C; adaxial winter and early spring leaves surrounding veins nearer RHS 186A and RHS 187D, with area between the veins nearest RHS N186A; abaxial winter and early spring leaves between RHS 187A and RHS 187B.

*Leaf margin*.—Serrulate becoming nearly rounded, pubescent.

*Leaf apex*.—Cuspidate becoming more crenate, pubescent.

*Leaf base*.—Cordate, auriculate with overlapping lobes.

*Leaf surface*.—Sparsely hirsutulous abaxial and adaxial; adaxial slightly vernicose when young in spring, matte when mature; abaxial vernicose all season.

*Leaf quantity*.—Dense, about 100 per plant.

Veins: Palmate, hirsutulous; ridged abaxial, slightly impressed adaxial.

*Vein color*.—On emerging spring foliage adaxial nearest a blend of RHS N187C and RHS 186D at base and nearest RHS N187A distally, with emerging spring abaxial nearest RHS N186D; mid-season and flowering time adaxial nearest RHS 183C proximally and distally nearest RHS N187A, mid-season and flowering time abaxial nearest RHS N186D; winter adaxial between RHS 180C and RHS 180D proximally and nearest RHS 186A distally with abaxial nearest RHS N186D.

Bracts: At main nodes of panicle, incised to five-lobed, about 13 mm long and 2.0 mm wide decreasing distally, with acute apices and lobes, base sessile and truncate.

*Bract color*.—Between RHS N186D and RHS 187D.

Petiole: Cylindrical, pubescent; up to about 19 cm long and 3 mm wide.

*Petiole color*.—Nearest RHS 187C in lower region and RHS 187B in upper portion.

Inflorescence: Mostly-vertical branched panicle, usually one panicle per main division, about 10 per plant; branches in proximal three quarters of the nodes; held at about 20 to 30 degree angle from vertical peduncle; lower branches about 3.5 cm long and about 0.5 mm diameter decreasing distally; panicle head average about 7.0 cm across and 70 cm tall; flowering starting in late spring to early summer lasting for about 4 weeks; no significant fragrance detected.

Peduncle: Stiff, round in cross section, densely hirsutulous, about 70.0 cm long and 6.0 mm in diameter at base; attitude semi-upright.

*Peduncle color*.—Between RHS 187B and RHS N186C proximally and nearest RHS 187A distally.

Pedicel: Round in cross section, hirsutulous, about 2.5 mm long and 0.5 mm diameter.

*Pedicel color*.—Nearest RHS N186C proximally and lightening to nearest RHS 182D distally before sepals.

Bracts: At panicle main nodes incised to five lobed, about 10 mm long and 2.0 mm wide decreasing distally, with acute apices and base sessile and truncate; color nearest RHS 187B.

Buds one day prior to opening: Ellipsoid, about 5.0 mm long and 3.0 mm diameter; hirsutulous.

*Bud color one day prior to opening*.—Basal portion nearest RHS 148B, becoming nearest RHS 159B in distal one half; with faint tinting of nearest RHS 185B.

*Bud color three days prior to opening*.—Nearest RHS 179C.

Flower: Perfect, campanulate, actinomorphic, about 9.0 mm long and 5.0 mm in diameter at face; individual flowers lasting about 4 days on plant or as cut flower; about 100 to 155 flowers per panicle; attitude semi-downwards.

Calyx: Five, apex acute, base fused in proximal half to form hypanthium; about 4.0 mm long and 4.0 mm wide.

*Calyx color*.—Abaxial base lighter and more green than RHS 153D and RHS 152D and more brownish grey than RHS 148D, distal two thirds cream-colored lighter than RHS 155D; adaxial color cream-colored lighter than RHS 155D and base of nearest RHS 139D.

Petals: Five, oblanceolate, acute apex and attenuate base, entire, about 5.5 mm long and 1.0 mm wide in middle.

*Petal color*.—White, lighter than RHS 155D.

Androecium:

*Filaments*.—Five, thin, about 5.0 mm long and less than 0.5 mm diameter; color white, lighter than RHS 155D.

*Anthers*.—Elliptical, about 1.5 mm long and 0.5 mm diameter, distinct, basifixed longitudinal; color nearest RHS N163B.

*Pollen*.—Abundant; color nearest RHS 16C.

Gynoecium: Two-beaked; bifid style with pistil split at ovary; 6.0 mm long.

*Ovary*.—Half-inferior, about 3.0 mm long and 2.5 mm diameter, pointed apex ending in style, base rounded, color nearest RHS 144C.

*Style*.—Two, split apart at apex of ovary; about 5.0 mm long and less than 0.5 mm diameter; slightly curving splitting apart about 3.0 mm at distal region; color white, lighter than RHS 155D.

*Stigma*.—Smaller than 0.5 mm diameter, globose; color lighter than RHS 155D.

Fruit: Two-beaked capsule, about 6 mm long and 3 mm in diameter at widest portion; color nearest RHS N199B when mature.

Seed: Ovoid, less than 1 mm long and wide; color black, nearest RHS 202A.

Disease and pest tolerance: The new plant grows best with ample moisture and drainage in either sun or shade. It is more tolerant of hot and humid environments than typical Coral Bells. Cold hardy from USDA zones 4 to 9. Other resistance and tolerance outside of that normal for *Heuchera* is not known.

I claim:

1. The new and distinct Coral Bells plant named *Heuchera* 'Grape Expectations' as herein described and illustrated with panicles of near white flowers and foliage changing colors throughout the seasons, with improved heat and humidity tolerance suitable for landscaping or as cut flower or foliage decoration.

* * * * *